(12) United States Patent
Daniel et al.

(10) Patent No.: US 10,468,125 B1
(45) Date of Patent: Nov. 5, 2019

(54) SYSTEM AND METHOD FOR DIAGNOSIS AND TREATMENT OF CARDIAC EPISODES

(75) Inventors: William C Daniel, Overland Park, KS (US); Dan Doherty, Dallas, TX (US)

(73) Assignee: Emerge Clinical Solutions, LLC, Dallas, TX (US)

( * ) Notice: Subject to any disclaimer, the term of this patent is extended or adjusted under 35 U.S.C. 154(b) by 36 days.

(21) Appl. No.: 13/250,609

(22) Filed: Sep. 30, 2011

Related U.S. Application Data

(63) Continuation-in-part of application No. 11/366,247, filed on Mar. 2, 2006, now abandoned.

(51) Int. Cl.
G06Q 10/00 (2012.01)
G16H 10/00 (2018.01)

(52) U.S. Cl.
CPC .................... G16H 10/00 (2018.01)

(58) Field of Classification Search
USPC .......................................... 705/2, 3
See application file for complete search history.

(56) References Cited

U.S. PATENT DOCUMENTS

| | | |
|---|---|---|
| 5,993,001 A | 11/1999 | Bursell et al. |
| 6,234,964 B1 | 5/2001 | Iliff |
| 6,621,918 B1 | 9/2003 | Hu et al. |
| 6,767,325 B2 | 7/2004 | Iliff |
| 6,988,088 B1 | 1/2006 | Miikkulainen et al. |
| 7,034,691 B1 | 4/2006 | Rapaport et al. |
| 7,213,009 B2 | 5/2007 | Pestotnik et al. |
| 7,321,861 B1 | 1/2008 | Oon |
| 7,436,311 B2 | 10/2008 | Rapaport et al. |
| 7,573,439 B2 | 8/2009 | Lau et al. |
| 7,598,028 B2 | 10/2009 | Macoska |
| 7,629,889 B2 | 12/2009 | Sachanandani et al. |
| 7,711,671 B2 | 5/2010 | Meyers |
| 7,723,050 B2 | 5/2010 | Urdea et al. |
| 7,733,224 B2 | 6/2010 | Tran |
| 7,916,014 B2 | 3/2011 | Rapaport et al. |
| 7,917,438 B2 | 3/2011 | Kenedy et al. |
| 2003/0104470 A1 | 6/2003 | Fors et al. |
| 2005/0131663 A1 | 6/2005 | Bangs et al. |
| 2009/0024553 A1 | 1/2009 | Angell et al. |
| 2009/0048866 A1 | 2/2009 | Mahesh et al. |
| 2009/0089392 A1 | 4/2009 | Fiedotin et al. |
| 2009/0248442 A1 | 10/2009 | Pacheco et al. |
| 2010/0030574 A1 | 2/2010 | Coe et al. |
| 2011/0077973 A1 | 3/2011 | Breitenstein et al. |
| 2011/0105852 A1 | 5/2011 | Morris et al. |

*Primary Examiner* — Valerie Lubin
(74) *Attorney, Agent, or Firm* — William H. Quirk; Jesse Frizzell; Rosenthal Pauerstein Sandoloski Agather LLP

(57) ABSTRACT

Methods of accelerating the adoption of a medical treatment by health care providers are disclosed. The methods include providing to a health care provider a set of selectable criteria for determining whether a specific medical treatment is indicated for a particular patient, analyzing the criteria selected, and indicating to the health care provider whether the medical treatment is indicated. A specific method suitable for addressing Heart Failure-Sudden Cardiac Death (HF-SCD) prevention is provided.

14 Claims, 10 Drawing Sheets

Sudden Cardiac Arrest Risk Assessment

- ◉ EF <= 35% (measured by echo, radionuclide, angiography)*
  With either:
  -- NYHA Class II-III HF, Non-Ischemic Dilated Cardiomyopathy > 9 months
  -- NYHA Class II-III HF, Prior Myocardial Infarction, Ischemic Dilated Cardiomyopathy
- ○ EF <= 30%, Prior MI > 40 days, *excluding* patients with NYHA Class IV Heart Failure *
- ○ No EF Measurement Recorded but Patient Meets HF or Post MI Criteria Action:
- ○ * -- if Last EF Measurement not within 6 months Order 2D Echo or ○ MUGA for EF Measurement
- ○ Provide more information and follow up with [ ]
- ◉ Nurse education; show video; schedule ICD
- ○ Exclusion ACTION: Nurse education; show video; schedule ICD

FIG. 4

Sudden Cardiac Arrest Risk Assessment

- ○ EF <= 35% (measured by echo, radionuclide, angiography)*
  With either:
  -- NYHA Class II-III HF, Non-Ischemic Dilated Cardiomyopathy > 9 months
  -- NYHA Class II-III HF, Prior Myocardial Infarction, Ischemic Dilated Cardiomyopathy
- ◉ EF <= 30%, Prior MI > 40 days, *excluding* patients with NYHA Class IV Heart Failure *
- ○ No EF Measurement Recorded but Patient Meets HF or Post MI Criteria Action:
- ○ * -- if Last EF Measurement not within 6 months Order 2D Echo or ○ MUGA for EF Measurement
- ◉ Provide more information and follow up with [CHF MD]
- ○ Nurse education; show video; schedule ICD
- ○ Exclusion ACTION: Provide more information and follow up with CHF MD

Sudden Cardiac Arrest Risk Assessment

○ EF <= 35% (measured by echo, radionuclide, angiography)*
   With either:
   -- NYHA Class II-III HF, Non-Ischemic Dilated Cardiomyopathy > 9 months
   -- NYHA Class II-III HF, Prior Myocardial Infarction, Ischemic Dilated Cardiomyopathy ○ EF <= 30%, Prior MI > 40 days, *excluding* patients with NYHA Class IV Heart Failure *

● No EF Measurement Recorded but Patient Meets HF or Post MI Criteria

Action:
● Order 2D Echo or  ○ MUGA for EF Measurement

[OK] [Cancel]

ACTION: Order 2D Echo for EF Measurement.

FIG. 7

Sudden Cardiac Arrest Risk Assessment

● EF <= 35% (measured by echo, radionuclide, angiography)*
   With either:
   -- NYHA Class II-III HF, Non-Ischemic Dilated Cardiomyopathy > 9 months
   -- NYHA Class II-III HF, Prior Myocardial Infarction, Ischemic Dilated Cardiomyopathy ○ EF <= 30%, Prior MI > 40 days, *excluding* patients with NYHA Class IV Heart Failure *

○ No EF Measurement Recorded but Patient Meets HF or Post MI Criteria

Exclusion Criteria

○ ESRD on dialysis
● Severe diabetes with end organ complications
○ Paraplegia or previous CVA
○ Age > 85 but still fairly active, mentally and physically

Action:
* -- If Last EF Measurement not within 6 months
○ Order 2D Echo or  ○ MUGA for EF Measurement
○ Provide more information and follow up with [ ]
○ Nurse education; show video; schedule ICD
● Exclusion
   ○ Temporary
      Contraindications that Temporarily prevent
      patient from entering SCA protocol.
   ● Relative
      Includes chronic debilitating conditions in which life
      expectancy is greater than 12 months buy overall
      quality of life may not be adequate to warrant ICD.
   ○ Absolute
      Quality of Life Indicators i.e. those conditions in which
      quality of life is so poor that prolonging it with an ICD
      would not be appropriate for the patient.

[OK] [Cancel]

ACTION: M.D. Review and determine patient care path. Document Exclusion or Continue SCA Protocol.

SYSTEM AND METHOD FOR DIAGNOSIS AND TREATMENT OF CARDIAC EPISODES

CROSS REFERENCE TO RELATED APPLICATION

This application claims the benefit under 35 USC § 120 of co-pending U.S. patent application Ser. No. 11/366,247 filed Mar. 2, 2006, the full disclosure of which is incorporated herein by reference.

STATEMENT REGARDING FEDERALLY SPONSORED RESEARCH

Not Applicable.

BACKGROUND OF THE INVENTION

1. Field of the Invention

The present invention is directed generally to the use of medical advances by the medical community, particularly as relates to potentially serious cardiovascular episodes such as possible heart failure and/or sudden cardiac arrest and, more specifically, to a system and method for assisting health care providers in properly diagnosing and responding to such cardiovascular episodes.

2. Description of Related Art

The present invention provides a method that allows health care providers to easily determine whether and when particular medical treatments or therapies are indicated, preferably in the area of Sudden Cardiac Arrest (also known as Sudden Cardiac Death) and other potentially serious cardiovascular episodes and risks.

Between 300,000 and 400,000 people die each year from Sudden Cardiac Arrest (SCA), which describes the abrupt loss of heart function in a human being. As the name suggests, SCA strikes suddenly, providing no warning to the affected individual or his doctors. The victims are as likely to be male as female, and may or may not have a previously diagnosed heart disease. Death generally occurs within minutes after symptoms of SCA first appear.

Despite the foregoing, SCA is treatable if the appropriate treatment is applied quickly enough following the onset of symptoms. Treatment commonly involves the use of a defibrillator, which delivers an electrical shock to the heart in order to restore a normal heartbeat. In most instances of SCA, however, by the time a defibrillator is on the scene, it is already too late to save the patient.

For individuals at high risk of suffering SCA, a more advanced treatment or prevention device is available, namely an Implantable Cardioverter Defibrillator (ICD). An ICD, generally implanted near the shoulder of a person at risk for SCA, provides the best chance of surviving an SCA event. The ICD monitors the patient's rhythm in a real-time, ongoing fashion. Should the patient experience an arrhythmia, the ICD paces the heart, restoring the proper rhythm. When necessary, the ICD also acts as a defibrillator, returning the heart to its normal rhythm by providing an electrical shock thereto. An ICD may terminate arrhythmias as much as 99% of the time, increasing the survival rate for SCA from about 10% or less to about 99%.

In an exemplary embodiment, the present invention provides a convenient, accurate way for a health care provider to assess the risk of SCA in an individual patient, and therefore to assess whether implantation of an ICD is indicated for that individual. The present invention preferably provides such a method in the form of computer software that is readily utilized by doctors, nurses, and other healthcare providers.

SUMMARY OF THE INVENTION

The present invention is directed to a method of accelerating the adoption of a medical treatment by health care providers. The method includes providing to a health care provider a set of selectable criteria for determining whether a specific medical treatment is indicated for a particular patient, analyzing the criteria selected, and indicating to the health care provider whether the medical treatment is indicated.

The present method is further directed to analyzing exclusion criteria when a patient is determined to be unsuitable for inclusion in a particular medical treatment. The present method provides that the exclusion criteria be categorized as temporary, relative, or absolute. In the case of temporary exclusion criteria, the patient may be included in the medical treatment once the temporary exclusion criteria are dealt with. In the case of relative exclusion criteria, a physician will further evaluate a patient in order to determine whether the patient should be included in the medical treatment. In the case of absolute exclusion criteria, the health care provider is instructed that the patient should not be included in the medical treatment.

One exemplary embodiment of the present invention is directed to determining the suitability of a patient for receiving an ICD.

A further exemplary embodiment of the present invention is directed to a broader (more detailed) approach to the treatment/prevention of Heart Failure & Sudden Cardiac Death, while some embodiments are directed to procedures relating to potentially serious cardiovascular episodes in general.

Many other objects, features, advantages, benefits, improvements and non-obvious unique aspects of the present invention, as well as the prior problems, obstacles, limitations and challenges that are addressed, will be evident to the reader who is skilled in the art, particularly when this application is considered in light of the prior art. It is intended that such objects, features, advantages, benefits, improvements and non-obvious unique aspects are within the scope of the present invention, the scope of which is limited only by the claims of this and any related patent applications and any amendments thereto.

To the accomplishment of all the above, it should be recognized that this invention may be embodied in the form illustrated in the accompanying drawings, attention being called to the fact, however, that the drawings are illustrative only, and that changes may be made in the specifics illustrated or described.

BRIEF DESCRIPTION OF THE DRAWINGS

FIG. 4 is a screenshot illustrating one aspect of a method developed according to the teachings of the present invention.

FIG. 5 is a screenshot illustrating another aspect of a method developed according to the teachings of the present invention.

FIG. 6 is a screenshot illustrating another aspect of a method developed according to the teachings of the present invention.

FIG. 7 is a screenshot illustrating another aspect of a method developed according to the teachings of the present invention.

FIG. 13 is a screenshot illustrating a order confirmation reporting window 370 of an alternative embodiment developed according to the teachings of the present invention.

DETAILED DESCRIPTION OF PREFERRED EMBODIMENTS

The present invention provides and enables straightforward methods and systems by which healthcare professionals can determine whether, when and how particular types of medical tests, diagnostics, preventions, therapies or treatments (collectively, for reference, "procedures") are indicated for a particular patient. Preferred embodiments are particularly adapted for use in guiding and supporting the clinical decision process in relation to patients who are thought to have suffered from or be at significant risk of suffering from a serious episode, particularly a serious cardiac and/or cardiovascular episode.

Embodiments of the present invention are particularly beneficial for use in conjunction with new or advanced procedures, although it is recognized that "new" and "advanced" characterizations are relative and should not be viewed as limiting for purposes of these descriptions. Rather, it should be understood that aspects of various embodiments may be used with procedures that may only be considered "advanced" relative to procedures more than fifty years old. Indeed, "new" procedures should be understood to include procedures that have only been known for five months as well as procedures that have been known for five decades, or perhaps longer.

For purposes of these descriptions, absent other express or implied limitation, the phrases "cardiac episode" and "cardiovascular episode" should both be understood in a very broad sense, generally both of which should be understood as referring to the occurrence or suspected occurrence of any potentially serious cardiac and/or cardiovascular disorder, disease, injury or other condition, including without limitation one or more of sudden cardiac death, cardiac arrest, myocardial infarction, congestive or other heart failure, cardiomyopathy, angina, cardiac arrhythmia, coronary artery disease, peripheral vascular disease or any other potentially serious cardiac and/or cardiovascular episode.

Figure 1:
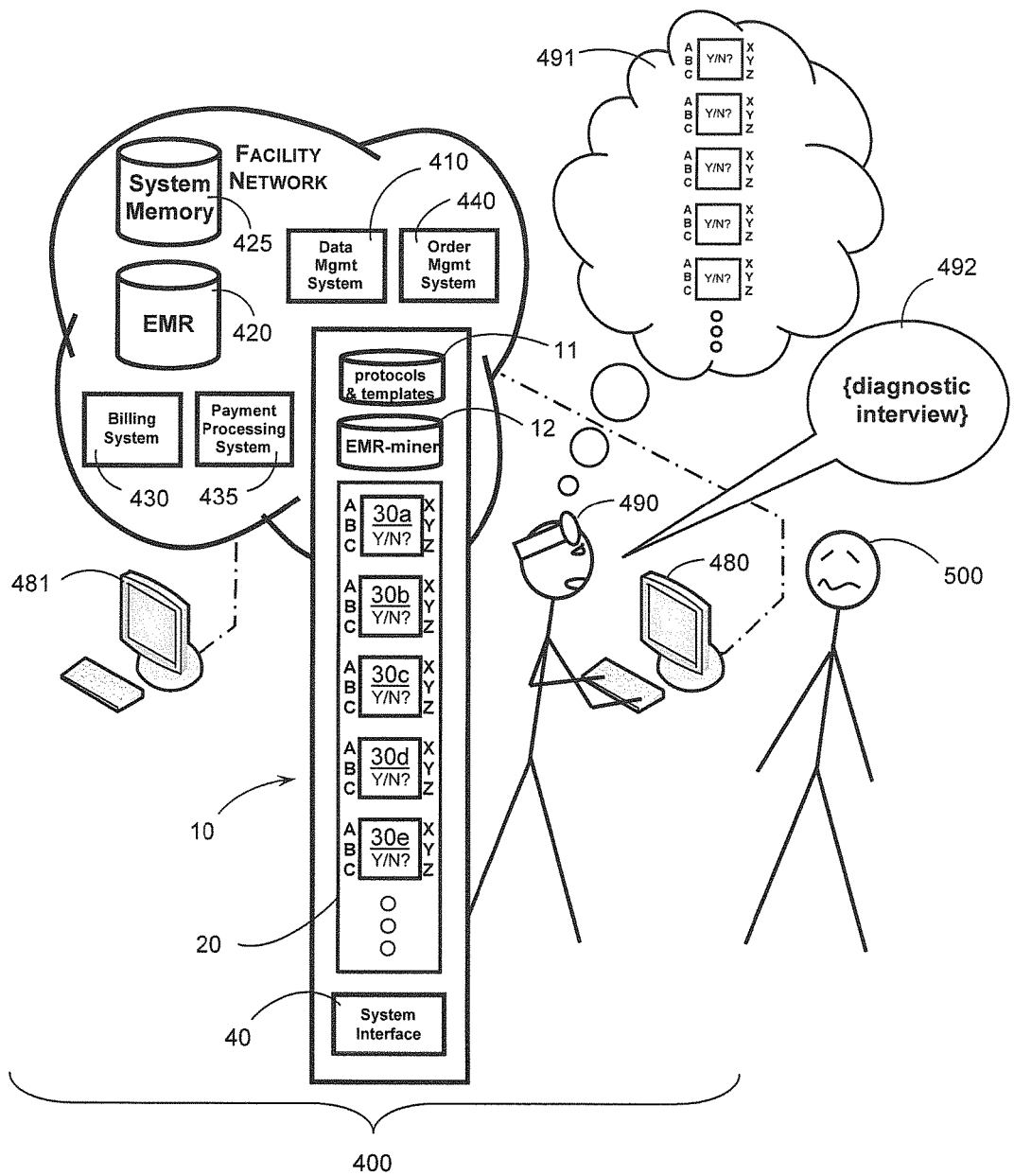
FIG. 1 is a schematic illustration of a typical preferred embodiment 10 of the present invention deployed as a middleware solution for supporting cardiac and cardiovascular care and clinical decisions by Professional Caregiver 490 relative to patient 500.

With reference to FIG. 1, there is shown a symbolic representation of a typical preferred embodiment of the present invention deployed as a middleware system 10 for supporting cardiac care decisions and other clinical decisions by Professional Caregiver 490 relative to patient 500. System 10 and the support it provides are both knowledge-based and flexibly-intelligent. The system 10 is knowledge-based in that guidance and recommendations are provided to Caregiver 490 based on both pre-existing and newly-entered information about patient 500. Pre-existing information is gathered by background processes of system 10 from the data network 400 for the given facility and/or healthcare network, which is preferably a secure network that stores pre-existing information in both Electronic Medical Records 420 and other memory systems 425. The support provided by system 10 is also flexibly-intelligent in that it predicts answers to various queries while also allowing for the information gathered from the facility network system 400 to be augmented, updated, verified or overridden by information newly-entered by Professional Caregiver 490, to the extent permitted by and consistent with a rules-based engine 20 of system 10.

As depicted by the graphic thought process 401 in FIG. 1, caregiver 490 is generally trained to consider various factors A, B and C in determining whether, when and how to perform various procedures relative to patient 500. Although previously gathered information can be helpful, such procedural determinations are typically ultimately based on the caregiver's personal observation and on the answers to questions explored during diagnostic interviews 492 with the patient 500 or other persons with pertinent knowledge.

To facilitate and support caregiver decisions about various procedural decision points 30a-30e that have been chosen and tailored according to the present invention, preferred embodiments of the present invention include software referenced as rules engine 20 that is programmed to provide, generally, for the determination of such decision points 30a-30e. Decision points 30a-30e are more numerous than five decision points in preferred embodiments, but points 30a-30e are shown for illustration. In some preferred embodiments, each such decision point 30a-30e, individually or together with other ones of decision points 30a-30e, corresponds to whether or not one or more particular procedures are indicated. With each such decision point 30a-30e, system 10 preferably also makes and/or helps the caregiver decide secondary choices and/or detail steps X, Y and/or Z. It should be understood that the graphical representation of secondary choices and/or detail steps X, Y and Z is an exemplary reference to any number of such secondary choices and/or detail steps that are secondary to each of the corresponding procedural decision points 30a-30e, which should be followed if the particular corresponding procedure is or is not indicated.

In a preferred embodiment of the present invention, the method and system 10 are provided via computer software, either via the internet, via a stand-alone software application operating independently or in connection with other software systems, or some combination of the two. Some preferred embodiments may be characterized as middleware in that they are adapted to interface with and work in conjunction with an independent data management system 410 and associated electronic medical records ("EMR") systems 420 of the corresponding healthcare facility and/or healthcare network 400. It is contemplated, however, that any other suitable means, even possibly in paper form, may also be used in alternative embodiments, all to the extent permitted within a proper construction of the scope of the claimed invention.

As well, embodiments may come in any known form and may also be implemented by hardware, software, scripting languages, firmware, middleware, microcode, hardware description languages, and/or any combination thereof. When implemented with coded programming, it should also be understood that the program code or code segments to perform the necessary steps or tasks of alternative embodiments may be coded in solid state or may be stored in a machine-readable medium such as a computer storage medium. A code segment or machine-executable step or instruction may represent a procedure, a function, a subprogram, a program, a routine, a subroutine, a module, a software package, a script, a class, or any combination of instructions, data structures, and/or program statements. Executable code segments may also be coupled to other code segments or to a hardware circuit by passing and/or receiving information, data, arguments, parameters, and/or memory contents, which may be passed, forwarded, or transmitted via any suitable means including memory sharing, message passing, token passing, network transmission, etc.

With reference again to FIG. 1, a particularly preferred embodiment is provided in the form of a software middleware system 10 that is installed and adapted to interact with the databases, servers and terminals 480-481 of a data management system 410 of a medical facility or analogous computerized medical network 400. Such system 10 is implemented and adapted to support caregivers by guiding them through a series of diagnostic questions A, B, and C in order to resolve the particular corresponding decision point 30a-30e. It should be understood that the graphical representation of diagnostic questions (or factors) A, B and C is an exemplary reference to any number of diagnostic questions and associated algorithmic logic necessary for resolving each respective decision point 30a-30e, which in turn depend on the particular decision point and the chosen methodology for making that decision according to the present invention. As depicted by the graphical correlation with the thought process 401, some preferred embodiments of such decision points 30a-30e are somewhat parallel to the various procedural decisions that caregiver 490 is generally trained to consider in determining whether, when and how to perform various procedures relative to patient 500, to aid caregiver 490 in making decisions relative to care of patient 500.

Further, system 10 is implemented and adapted to support caregiver 490 in methodically advancing through decision points 30a-30e, while simultaneously running background processes to mine for additional relevant data stored in the facility's EMR system 420. While the caregiver 490 is guided through questions A, B, C corresponding to each decision point, system 10 uses the additional relevant data mined from the EMR system 420 to propose and/or provide predicted answers to some or all of the same questions A, B, C. Once each question for a particular decision point 30 is completed or otherwise satisfied, generally either by a new entry by the caregiver 490 or by the caregiver's acceptance or validation that default answers or the answers derived from the EMR system 420 can be used, system 10 can then make final recommendations as to patient care for the corresponding decision point 30. At various opportunities throughout the overall process, system 10 allows caregiver 490 to supplement, validate and/or predict final entries for each applicable question A, B, C, as well each secondary consideration X, Y, Z.

Preferably, to provide evidence-based caregiver support for clinical decisions, system 10 is further adapted to provide the same access to clinical information, support and resulting recommendations. and to facilitate and enable final order execution relative to a particular patient 500. through multiple convenient terminals 480, 481, which are conveniently located in close proximity to multiple possible points of care for patient 500. Software system 10 preferably uses the existing information systems of facility 400 to interface with the facility EMR system 420 and data management system 410. The integration with system 400 preferably allows system 10 to safely locate, interpret and extract patient data from electronic medical records 420 and to create readily-executable orders for physician 490 to consider, revise, reject or approve in the management of the patient's heart and vascular conditions.

Figure 2:
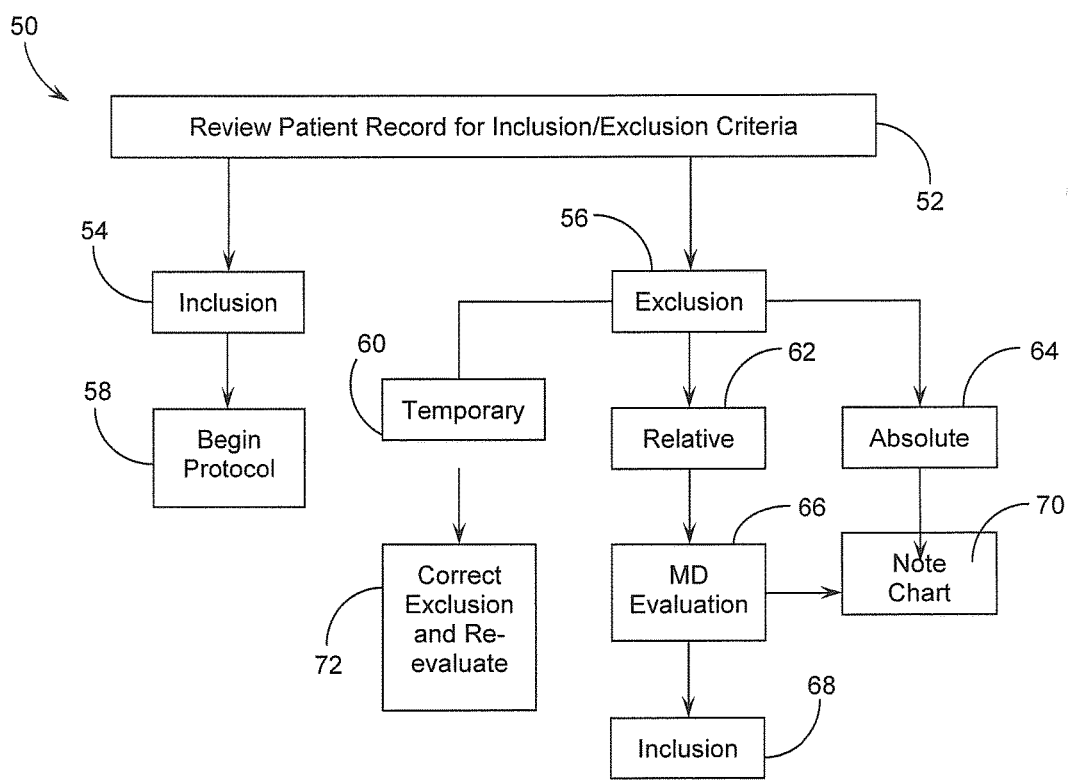
FIG. 2 is a schematic diagram of the method of a preferred embodiment according to the present invention.

FIG. 2 provides a schematic overall diagram of a general method 50 according to the present invention. The method includes, generally, determining whether a particular patient meets inclusion or exclusion criteria for the procedure in question, beginning the procedure if inclusion criteria are met (or, alternatively, if exclusion criteria are not met), and evaluating the patient further if exclusion criteria are met.

Step 52 of the method shown in schematic form in FIG. 2 includes reviewing a patient's records in order to determine whether that patient meets the criteria for inclusion with respect to a procedure, or, alternatively, whether the patient meets the criteria for exclusion with respect to the same. The inclusion or exclusion criteria for a particular procedure will vary depending on the particular procedure at issue, and are determined by doctors or other medical specialists with the appropriate level of expertise in the area to which the procedure pertains. Preferably, a health care provider attempting to determine whether a procedure is indicated in a particular case will be provided with a list or series of inclusion or exclusion criteria via a computer. The health care provider may then select the criteria that apply to a given patient by a variety of known methods, including clicking on a checkbox or radio button next to criteria that apply, or selecting applicable criteria from a dropdown menu onscreen. Once the health care provider has selected the applicable criteria, the computer program will analyze the selections and instruct the health care provider as to whether the medical procedure is indicated.

If the medical procedure is indicated, that is, if the patient meets the inclusion criteria or, alternatively, does not meet the exclusion criteria, the health care provider is notified that the procedure is indicated for that patient. This step is shown by way of box 54 in schematic FIG. 2. Once it has been determined that a particular patient is to be included in a procedure, the procedure protocol commences, as shown by way of box 58 in schematic FIG. 2.

The step of the present method indicated by box 58 in FIG. 2 includes, generally, a number of additional steps that make up the protocol at issue. The particular steps involved will vary from protocol to protocol, though there may also be a degree of overlap between some or all of the protocols. For example, a first step in the protocol may be to provide patient education concerning the procedure. This allows the patient to become familiar with the risks versus benefits of the procedure in question. After the education has been provided, the patient may elect to undergo the procedure, may hold out for additional information, or may decline the procedure altogether. If additional educational materials are requested by the patient, these may also be provided as part of the step indicated by box 58 of FIG. 2. Once the patient decides to proceed with the procedure, then additional steps within box 58 may include referral to the appropriate physicians or departments for review of the case and preparation for a procedure, scheduling the procedure itself, meetings between the physician who will be performing the procedure and the patient, performance of the procedure, post-procedure care of the patient, discharge from the hospital (in the event the patient is hospitalized), and the like. In a preferred embodiment of the invention, each of these steps incorporated within broad box 58 of FIG. 2 is provided to a health care provider via a computer system, and the health care provider can then iteratively perform the various steps, indicating the successful completion or outcome of each step in order to be further instructed by the computer software. Further features of the present method will become apparent during the discussion of an exemplary embodiment of the present invention, below.

If it is determined that a patient meets the exclusion criteria for a particular procedure, or, alternatively, does not meet the inclusion criteria, then the analysis proceeds as shown via box 56 in FIG. 2. A health care provider may then wish to determine whether the exclusion from the procedure is temporary, relative, or absolute, as indicated by boxes 60, 62, and 64 of FIG. 2.

Temporary exclusions, indicated by box 60 in FIG. 2, are those that temporarily prevent the patients from being included in a given procedure. For example, a patient may have an existing infection that makes the procedure more dangerous, but may be perfectly well suited for the procedure once the infection has been treated and is no longer an issue. Further, it may be that a given course of drugs or medications prescribed to the patient prevent that patient's inclusion in a given procedure, but in the event that the drugs are only taken for a limited time, the patient may be well suited for the procedure once the drugs or medications are titrated to appropriate doses. In the case of a relative exclusion, then, once the exclusion is no longer in place, the patient may be included in the procedure. In a preferred embodiment of the invention, a health care provider is notified via computer whether exclusions discovered in step 52, above, are temporary, and what further actions may be taken to ensure inclusion in the procedure. Typically, the action to be taken includes re-evaluation of the patient once the temporary exclusion is no longer an issue.

Relative exclusions, indicated by box 62 in FIG. 2, are those exclusions that are not temporary (i.e., they will remain at issue), but with respect to which a health care provider may well decide that inclusion in a procedure is still the best course to pursue. For example, the age of a patient may be a relative exclusion. With respect to some treatments, therapies or other procedures, patients over a given age may be poorly suited for inclusion, but a particular individual may be healthy enough that a health care provider opts to select inclusion regardless (shown by box 68 of FIG. 2). Other medical conditions, such as organ failure, diabetes, and the like, may be such that the quality of life reasonably expected to be achieved by the procedure does not warrant inclusion of the patient in the procedure. In such an instance, a note may be made in the patient's chart indicating that inclusion in the procedure is not warranted (shown by box 70 in FIG. 2). In a preferred embodiment of the invention, information regarding relative exclusions is provided to a health care provider via a computer in such a manner that the health care provider can easily select which exclusions apply and analyze the various factors that may indicate inclusion despite the existence of relative exclusions, or may indicate exclusion from the procedure altogether.

Absolute exclusions (shown by box 64 of FIG. 2), are those that indicate that a particular patient should not be included in a given procedure. Often, absolute exclusions include quality of life indicators, such as advanced metastatic cancer, severe dementia, and the like, which make it inappropriate to prolong the patient's life using the particular procedure at issue. In the event of an absolute exclusion, a health care provider may simply note the patient's chart (as shown by box 70 of FIG. 2), indicating that the patient's suitability for a particular procedure was assessed and that the patient is not well suited for the procedure. In a preferred embodiment of the present method, a health care provider is provided with information concerning absolute exclusions via computer.

As discussed above, the present method is adaptable for use with a wide variety of medical treatments, therapies or other procedures. Any medical procedure, now existing or developed in the future, may in fact be susceptible to the present method. The following is a detailed discussion of the present method as applied to Sudden Cardiac Arrest (SCA).

Figure 3:
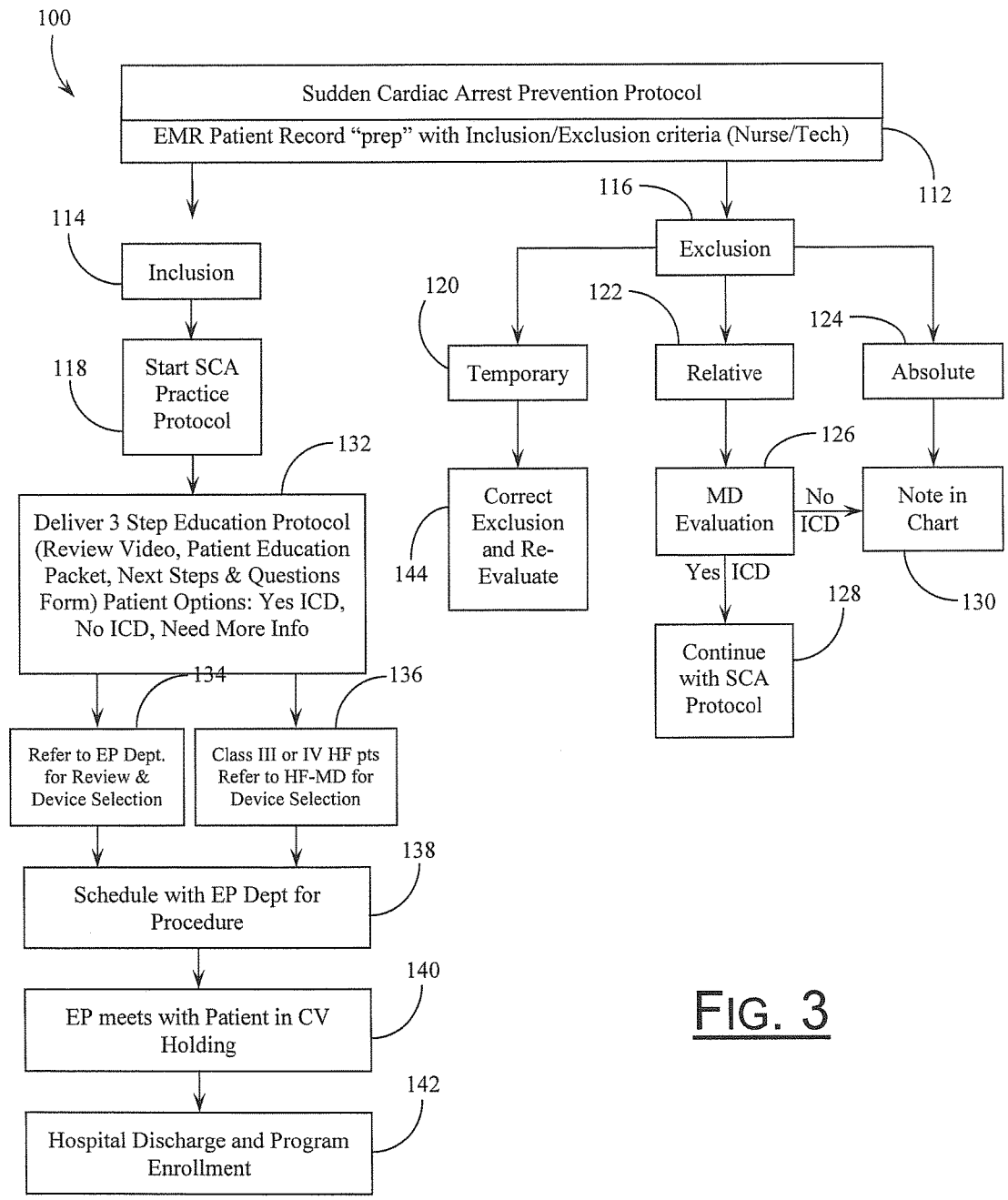
FIG. 3 is a schematic diagram of one embodiment of a method developed according to the teachings of the present invention.

FIG. 3 provides a schematic of an exemplary SCA protocol developed in accordance with the teachings of the present method. The method includes the general steps described above, namely, determining whether a particular patient meets inclusion or exclusion criteria for the medical procedure in question, beginning the procedure if inclusion criteria are met (or, alternatively, if exclusion criteria are not met), and evaluating the patient further if exclusion criteria are met.

During analysis of inclusion or exclusion criteria, a step shown by box 112 of FIG. 3, a variety of factors specific to the particular therapy, treatment or other procedure at issue are assessed. With respect to SCA, for example, an inclusion criterion may be that the patient has an ejection fraction (EF) of less than or equal to 35%, along with either NYHA Class II or III Congestive Heart Failure (CHF), or a history of Coronary Artery Disease or Myocardial Infarction (CAD/MI). FIG. 4 provides an exemplary computer screen showing an implementation of this step of the present method. As can be seen, radio buttons are provided for a health care provider to select which criteria are present in a given patient. In the computer screen shown, the inclusion factor described above has been elected. The right-hand portion of the computer screen in FIG. 4 then provides the health care provider with possible actions to be taken. For example, if the last EF measurement is greater than six months old, the computer program requests that the health care provider order a 2D echo or MUGA for EF measurement. In the instance shown in the figure, the health care provider has selected the option of providing nurse education, showing a video to the patient, and then scheduling the implantation of an Implantable Cardioverter Defibrillator (ICD). Once this action is selected, the present method will remember the actions yet to be taken and walk the health care provider through future actions in a stepwise manner.

FIG. 5 provides the same exemplary computer screen as shown in FIG. 4, but wherein the health care provider has indicated that the patient's ejection fraction is less than or equal to 30%, that there has been a previous incidence of myocardial infarction more than forty days in the past, and that the patient has NYHA Class IV heart failure. As can be seen in the figure, the action provided indicates that the patient should be provided with additional information and should follow up with a doctor who specializes in congestive heart failure. After the follow up visit, the health care provider may determine whether it is appropriate to include the patient in the SCA protocol.

FIG. 6 provides the same exemplary computer screen of FIGS. 4 & 5, but wherein the health care provider has indicated that no EF measurement has been recorded, but that the patient meets the heart failure or post-MI criteria necessary for possible inclusion in the SCA protocol. As can be seen in the figure, the action required is that the health care provider orders a 2D echo or MUGA for EF measurement. Once the patient's EF has been determined, the patient may be reevaluated for inclusion in the SCA protocol.

The above provides an exemplary embodiment of the present invention for determining whether a patient meets inclusion criteria of the SCA protocol. As can be seen, the method is adapted to provide a health care provider with an easy, stepwise manner in which to enter information into a computer and receive, in turn, possible actions to be undertaken based on the health care provider's choices. Thus, a health care provider is provided with a way to assess the appropriateness of possible inclusion of a patient in the SCA protocol, or in other embodiments any other procedure, without having to know by memory each of the inclusion criteria and corresponding action choices. In this way, the present method facilitates the adoption of medical procedures.

In addition to analyzing inclusion criteria, a health care provider also analyzes exclusion criteria in Step 112 of FIG. 3. The health care provider may be provided with a list of possible exclusion criteria to select from. In the case of SCA, for example, potential exclusion criteria may include, for example, quality of life indicators, stage of heart failure, chronic obstructive pulmonary disease (COPD) with a history of oxygen dependence, end stage renal disease or dialysis, severe diabetes with complications, dementia, metastatic or other cancers, paraplegia, cerebral vascular accident (CVA), chronic or active infections, and the like. The health care provider may select one or more exclusion criteria, preferably from a list of such criteria provided to the health care provider via a computer.

FIG. 7 shows an exemplary computer screen wherein certain exclusion criteria are displayed. In the screen shown, for example, a health care provider has indicated that the patient has an ejection fraction (EF) of less than or equal to 30%, along with either NYHA Class II or III Congestive Heart Failure (CHF), or a history of Coronary Artery Disease or Myocardial Infarction (CAD/MI). The health care provider has further selected the radio button preceding the word "Exclusion," and the radio button preceding the word "Relative." This has resulted in relative exclusion criteria being displayed on the left hand side of the screen. The health care provider is then able to select the applicable relative exclusion criteria, if any, also by means of clicking on a radio button. In the screen shown, the health care provider has indicated that the patient has severe diabetes with end organ complications. Other relative exclusion criteria shown are ESRD on dialysis, paraplegia or previous CVA, and that the patient is over eighty-five years of age but still fairly active mentally and physically.

Similar to what is shown in FIG. 7, when a healthcare provider selects the radio button preceding the word "Temporary" under the category of exclusions, a list of temporary exclusion factors is provided on the left side of the screen, and the health care provider may select any applicable factors that apply to a given patient. Temporary exclusion factors for SCA include, for example, non-ischemic dilated cardiomyopathy, class II or III CHF, myocardial infarction within the past forty days, CABG or PTCA within three months, clinical symptoms of findings (such as angina) that may require revascularization, active infections, ICM with no ischemic workup within 12 months, suspected or possible severe carotid disease, absence of beta blocker or Ace inhibitor/ARB, and that the patient is currently being titrated on beta blocker. Other temporary exclusions may also be applicable.

Likewise, in the manner shown in FIG. 7, when a healthcare provider selects the radio button preceding the word "Absolute" under the category of exclusions, the health care provider is provided with a list of absolute exclusion factors on the left side of the screen, and the health care provider may select any applicable factors that apply to a given patient. Absolute exclusion factors include, for example, severe end stage cardiomyopathy, severe end stage COPD with oxygen dependence, severe dementia, metastatic cancer, extensive neurological deficits, irreversible brain damage from preexisting cerebral disease, any disease other than cardiac disease associated with a likelihood of survival less than one year, and patient refusal of an ICD implant. Any one of these factors is sufficient to prevent a patient from moving forward in the SCA protocol. Other absolute exclusion factors may also exist.

Returning now to FIG. 3, the schematic provided shows additional steps of an exemplary SCA protocol developed in accordance with the teachings of the present method. The method proceeds along one of two major paths, depending upon whether a given patient has been initially selected for inclusion or exclusion in the SCA protocol.

In the instance wherein a patient is selected for inclusion in the protocol (as shown by box 114 of FIG. 3), the SCA practice protocol itself commences (box 118). In the preferred protocol shown in the figure, the health care provider is directed to begin a 3-step educational protocol to educate the patient on the ICD. The educational process preferably includes an informational video, a patient education packet for the patient to take home and study, a description of the next steps in the process, a frequently-asked questions form, and an opportunity for the patient to ask questions of the health care provider. Once the educational process (box 132) is completed, the patient must then decide whether to proceed with the ICD implantation, or whether she requires more information prior to proceeding. If more information is required, the patient can be provided with additional information until she is comfortable enough to proceed with implantation of the device. Each of the steps shown by boxes 114, 118, and 132 are preferably provided to a health care provider via a computer system in accordance with the teachings of the present invention. Thus, a health care provider not intimately familiar with the education and preparation of patients selected to receive an ICD may be directed stepwise through the process by computer. This increases the likelihood that such a health care provider will opt to adopt the SCA protocol constructed in accordance with the present invention. The likelihood that patients who would benefit from an ICD are in fact informed of that option and make the decision that is most appropriate to them is therefore increased as well.

As further seen in FIG. 3, once the patient decides to proceed with the implantation of an ICD, the patient and doctor must select the ICD device most appropriate for that patient. Class III or IV CHF patients are preferably referred to HF-MD for device selection (as shown by box 136), whereas other patients are preferably referred to the EP department for device selection (box 134). Again, the health care provider is directed through the process by the present method, preferably implemented in the form of computer software.

Once the proper ICD device has been selected, the patient proceeds through the final three steps of the SCA protocol developed in accordance with the present method. The patient and health care provider schedule the implantation procedure with the EP department (box 138), the EP meets with the patient in CV holdings (box 140), and after the procedure the patient is discharged from the hospital and enrolled in the CareLink program (box 142). The health care provider preferably ensures that each of these steps is completed appropriately by use of the present invention.

In the instance wherein a patient has been excluded from the SCA protocol developed in accordance with the present method, the process takes the second path shown in the schematic diagram FIG. 3, beginning with box 116 labeled "Exclusion." As shown in the figure, the health care provider must determine whether the exclusion criteria met by a particular patient are temporary, relative, or absolute. An exemplary method of determining whether the exclusion criteria are temporary, relative, or absolute is described with respect to FIG. 7 above.

In the instance wherein a patient has exclusion factors that are determined to be temporary (box 120), the health care provider is preferably directed to correct the temporary exclusion factor and schedule the patient to be reevaluated with respect to suitability for inclusion in the SCA protocol. In some embodiments, the present method may provide guidance to the health care provider in terms of how to resolve the temporary exclusion. Once the temporary exclusion has been resolved, the patient may be reevaluated and, if appropriate, begin the SCA practice protocol (box 118).

In the instance wherein a patient has exclusion factors that are determined to be relative (box 122), the health care provider is directed to schedule an evaluation of the patient with an appropriate doctor. The doctor may then examine the patient, take the relative exclusion factors into consideration, and then determine whether or not the patient warrants inclusion in the SCA protocol despite the existence of the relative exclusion factors. If the patient is a good candidate for an ICD despite the existence of the relative exclusion factors (box 128), the patient begins the SCA practice protocol (box 118). If the patient is not a good candidate for an ICD, a note may be made in the patient's chart indicating that the patient has been evaluated and found unsuitable for an ICD (box 130).

In the instance wherein the patient is found to have absolute inclusion factors, then according to the exemplary SCA protocol shown in FIG. 3, the patient is not suited to receive an ICD. In this case, a note may be made in the patient's chart indicating that the patient has been evaluated and found unsuitable for an ICD (box 130).

During each of the steps shown in FIG. 3 and described above, the health care provider is guided by the present method, preferably by way of a computer running software designed to implement the present method. Thus, a health care provider who is not familiar with the SCA protocol described can nevertheless make an accurate assessment as to whether a patient is a good candidate for an ICD using the above process. The ease with which the health care provider can make this assessment will accelerate the adoption of the SCA protocol described, and increase the number of people who are identified as good candidates for an ICD and subsequently obtain an ICD.

Some preferred embodiments provide much of such functionality through a middleware system 10 such as graphically illustrated in FIG. 1, which is adapted to interface with the data management systems 410 to guide physician caregiver 490 through a care decision process involving decision points 30*a*-30*e* and related logic that are characteristic of rules engine 20. Through interaction with the network 400 of a healthcare facility or analogous healthcare network, system 10 prompts and causes guidance screen displays to be provided to caregiver 490 on any of the available secure terminals 480-481 of facility network 400, while simultaneously mining additional pertinent data from the corresponding EMR database 420 through interaction with the related management and processing systems 410, 430, 435 and 440.

System 10 preferably operates, and physician caregiver 490 accesses as much, through a graphic user interface home screen (or "HomePage") 300 and related secondary screens, pop-ups and the like that are merged with other interactive data presentations characterized by the network's data management system 410 and its associated EMR system 420.

Figure 11:
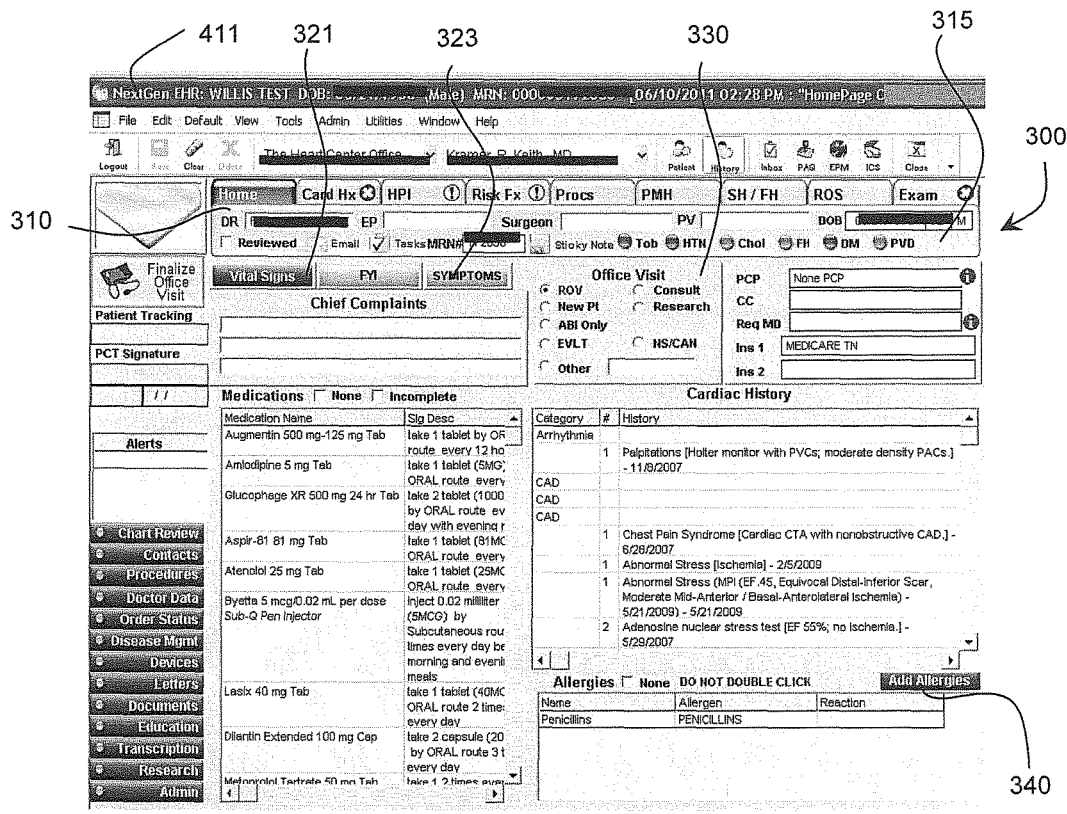
FIG. 11 is a screenshot illustrating a home screen 300 for various aspects of alternative embodiments developed according to the teachings of the present invention (portions of which are redacted in this description solely in order to minimize unintended disclosure of possible patient identifiers).
Figures 12A, 12B:
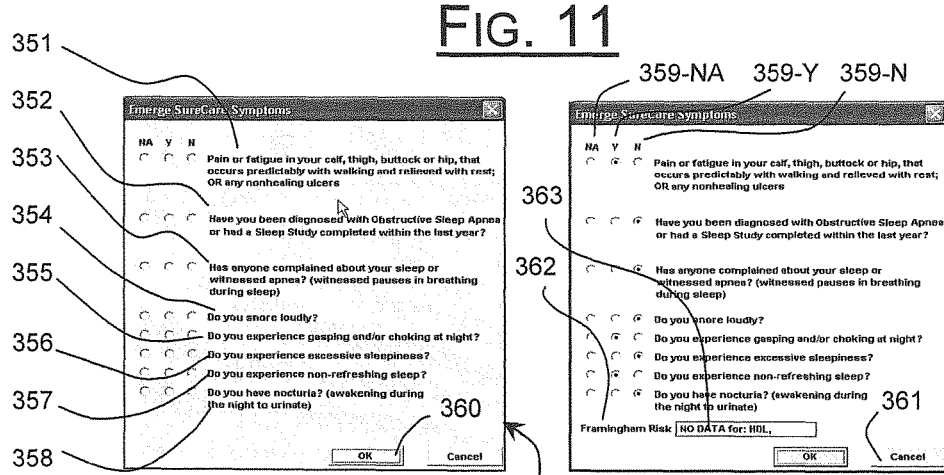
FIGS. 12A & 12B are screenshots illustrating a symptoms pop-up window 350 at two different stages of completion pursuant a preferred embodiment method of the present invention.
Figure 13:
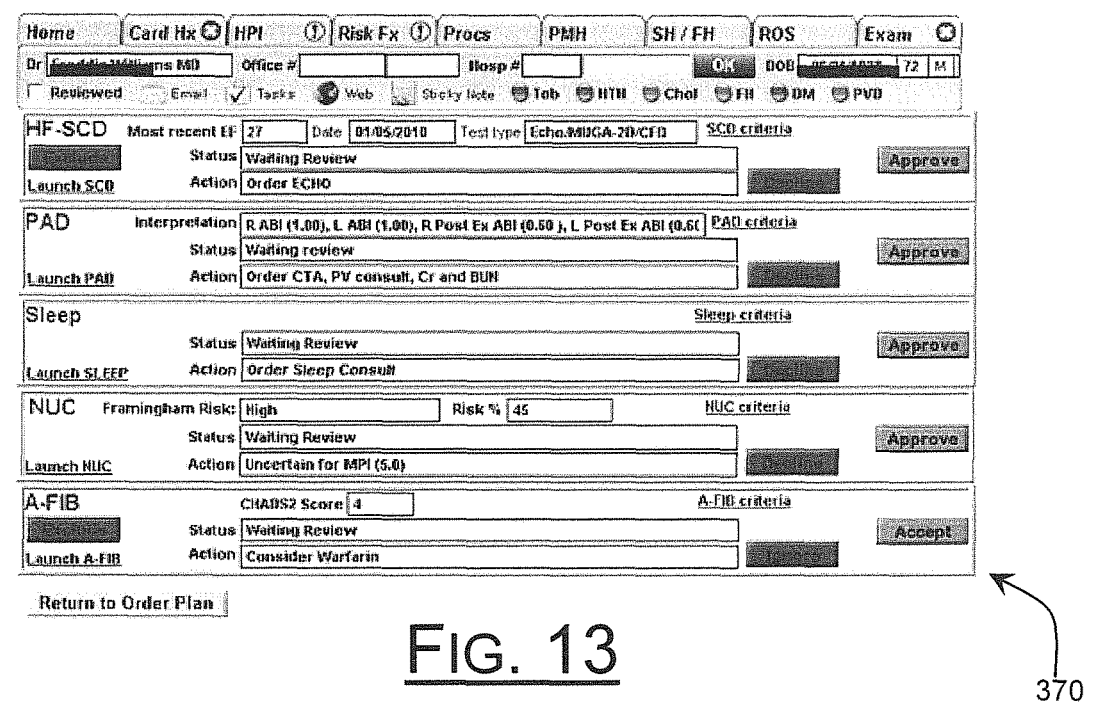

As represented in the screen shots of FIGS. 11-13, a particularly preferred implementation of the present invention is adapted through software technicians to interface with a popular knowledge-based data management system 410 commercialized under the "NextGen" product designation. Accordingly, a preferred embodiment of a HomePage 300 for system 10, as shown in the attached FIG. 11, includes various fields, windows, toolbars and the like (collectively, "regions") that are dictated entirely by the data management system 410 and that retain the same appearance as is familiar to users of such system 410, such as is the case with EMR menu bar 411 which is the uppermost section of HomePage 300. In contrast, other regions of HomePage 300 are given an appearance and corresponding functionality that is dictated by System 10 and its rules engine 20, such as is the case with a preferred rules engine index bar 310 that is displayed immediately under menu bar 411. Although automated integration is feasible in alternative embodiments, the integration of middleware system 10 with system 410 and other components of network 400 is preferably performed by specialized software technicians during an initial integration and discovery process that adapts system 10 such that its various fields, look-ups and parameters are mapped to integrate with the particular data structure and discrete data points of facility network 400. During such initial integration and discovery process, additional unique data accommodations are also created to the extent that required data points are missing from system 400 but are otherwise called for by the logic of system 10.

When middleware system 10 is integrated with data management system 410 and related systems of network 400, system 10 is then ready for use by caregivers 490—also referred to interchangeably as providers and/or patient care technicians (PCT) 490. In operation, system 10 then fully supports caregiver 490 through the diagnostic process of conducting diagnostic interviews 492 and making related observations in order to determine what procedures are indicated and/or should be recommended for patient 500, as well as how and when and other details relating to performing the procedures. Such diagnostic process is guided through use of HomePage 300 by PCT 490, while background processes of system 10 are mining the EMR 420 for pertinent data relating to the particular patient 500.

To use system 10 in such preferred embodiments, provider 490 uses one of the available terminals 480, 481 that is networked with facility network 400, preferably during each substantive encounter with patient 500. To commence such a use, PCT 490 clicks appropriate icons and the like to either create a new HomePage 300 that corresponds to patient 500, or to open a pre-existing one if it already exists on network 400. Alternative embodiments automatically locate and/or create such HomePage 300 based on intelligent machine recognition of the presence of patient 500 or a personal identifier accompanying patient 500 (such as a hospital wristband or a unique RFID tag assigned to patient 500).

In the process, PCT 490 is preferably prompted to first designate the type of patient encounter (i.e., "Office Visit") being conducted, by entering appropriate data in region 330 of HomePage 300. In the process, for a routine follow-up visit, preferred embodiments offer the streamlined options for the PCT 490 to just designate a focused type of follow-up patient encounter in order to streamline and simplify the level of prompting provided by system 10, and to watch for and make recommended procedure responses, to be in line with typical abbreviated follow-up visits with a patient 500 who has suffered or is thought to be at risk of suffering from a more particular type of cardiovascular episode. For instance, PCT 490 may designate either "ABI Only" or "EVLT" to cause system 10 to streamline and simplify the level of prompting provided by system 10 to be in line with follow-up visits with a patient 500 who has suffered or is thought to be at risk of suffering from peripheral arterial disease and potential cardiovascular blockage, respectively, as well as on related procedures. "EVLT" as such is indicative of EndoRevascularization (percutaneous or surgical) Laser Treatment, and selecting the "EVLT" option streamlines the prompting from system 10 to only focus on factors and recommendations relating to cardiovascular blockage and treatment. "ABI Only" streamlines the prompting to gather data about the patient's current ankle-brachial index, and to making related recommendations and/or orders relating to peripheral vascular disease and related vascular conditions.

Either through prompts or natural progression, PCT 490 then begins gathering vital signs for patient 500 and is guided through that process by clicking the "Vital Signs" button 321 of HomePage 300, which then causes a pop-up window to prompt and guide PCT through the process of gathering such vital signs as are required for rules engine 20 to make its recommendations. Until sufficient vital signs have been gathered and/or entered in such Vital Signs pop-up window, the "Vital Signs" button 321 is displayed in a manner to indicate that additional action is required under that pop-up window, such as by displaying the button 321 in the color red or with another alert condition.

Whenever the Patient's HomePage 300 is created or accessed by system 10 and/or PCT 490, the rules engine 20 of the middleware system 10 is preferably adapted to automatically process the data populated and/or entered in the various fields on HomePage 300, in order to intelligently guide and support PCT 490 through both diagnostic processes and related ordering processes, to determine and propose recommended ordering details and to cause the ordered procedures to be executed when validated (i.e., approved) by PCT 490. Throughout operation of system 10 during each patient encounter, system 10 is also adapted to create and retain (or to cause other processes to create and retain) hidden history files and/or hidden audit trails to enable caregiver 490 or network management or other interested parties to later conduct retrospective and/or systemic evaluations of the care of patient 500 and/or the quality of care being provided through PCT 490 or any particular grouping of caregivers, such as through the entire facility network 400.

Cardiac Protocol

While the above descriptions identify basic steps associated with a preferred embodiment of the present invention, particularly with reference to the identification of candidates for the receipt of an ICD, it should be understood that alternative embodiments include or enable additional, alternative and more detailed queries, steps and processes. Such alternatives, for instance, can be made to address the acquisition of additional patient test results, the preparation of the patient for a better inclusion or exclusion decision, and/or the possible combination of an ICD or other cardiac procedure with still further cardiovascular treatment protocols.

One particularly preferred alternative embodiment capitalizes on the SureCare software product (referred to as the "SureCare System" for purposes of this description), which is commercially available in the United States as of the filing date of this description.

Figure 8:
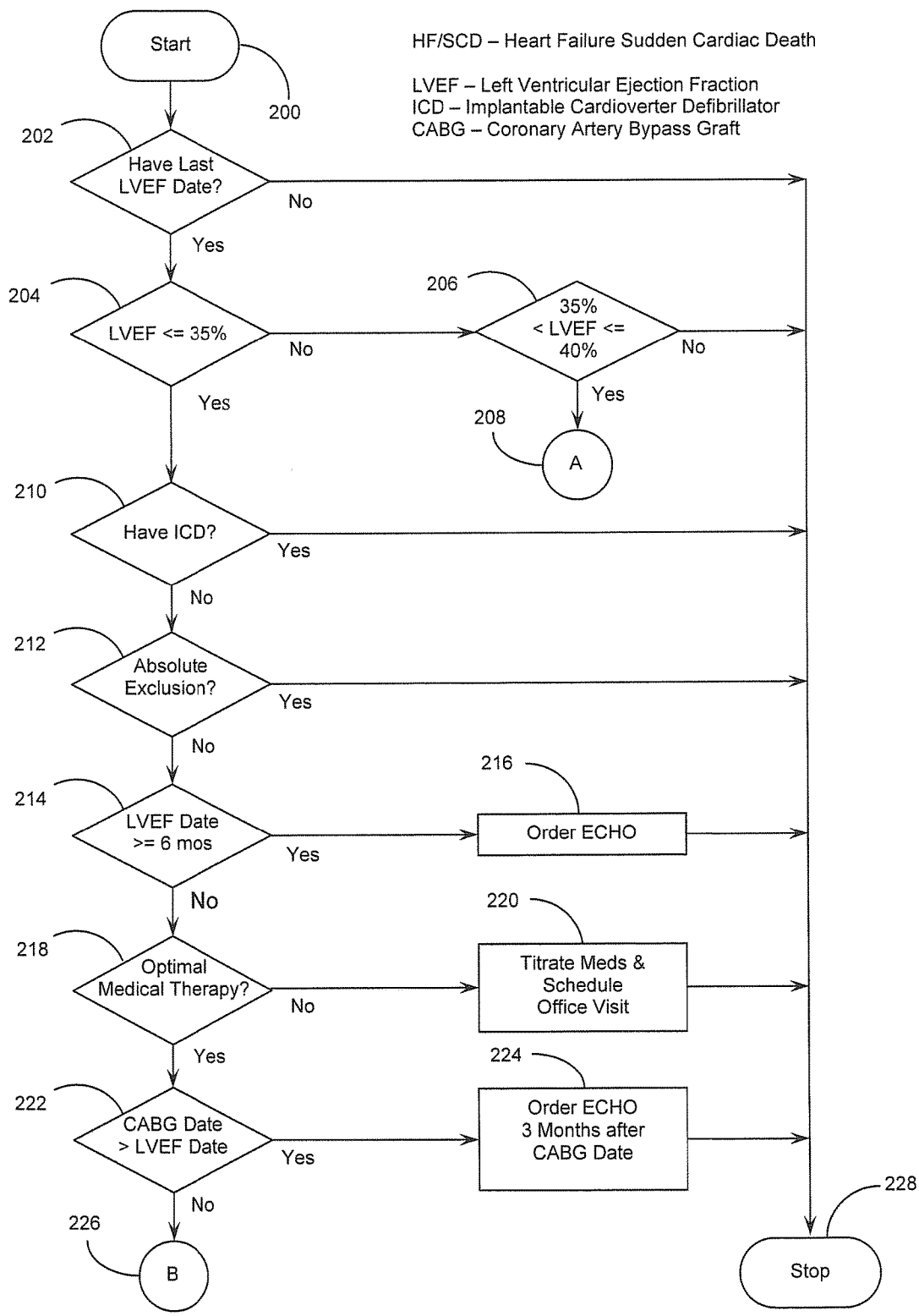
FIGS. 8-10 are schematic flow diagrams of method steps of an alternative embodiment of the present invention associated with a sudden cardiac episode diagnosis, prevention and treatment protocol and related modules.
Figure 9:
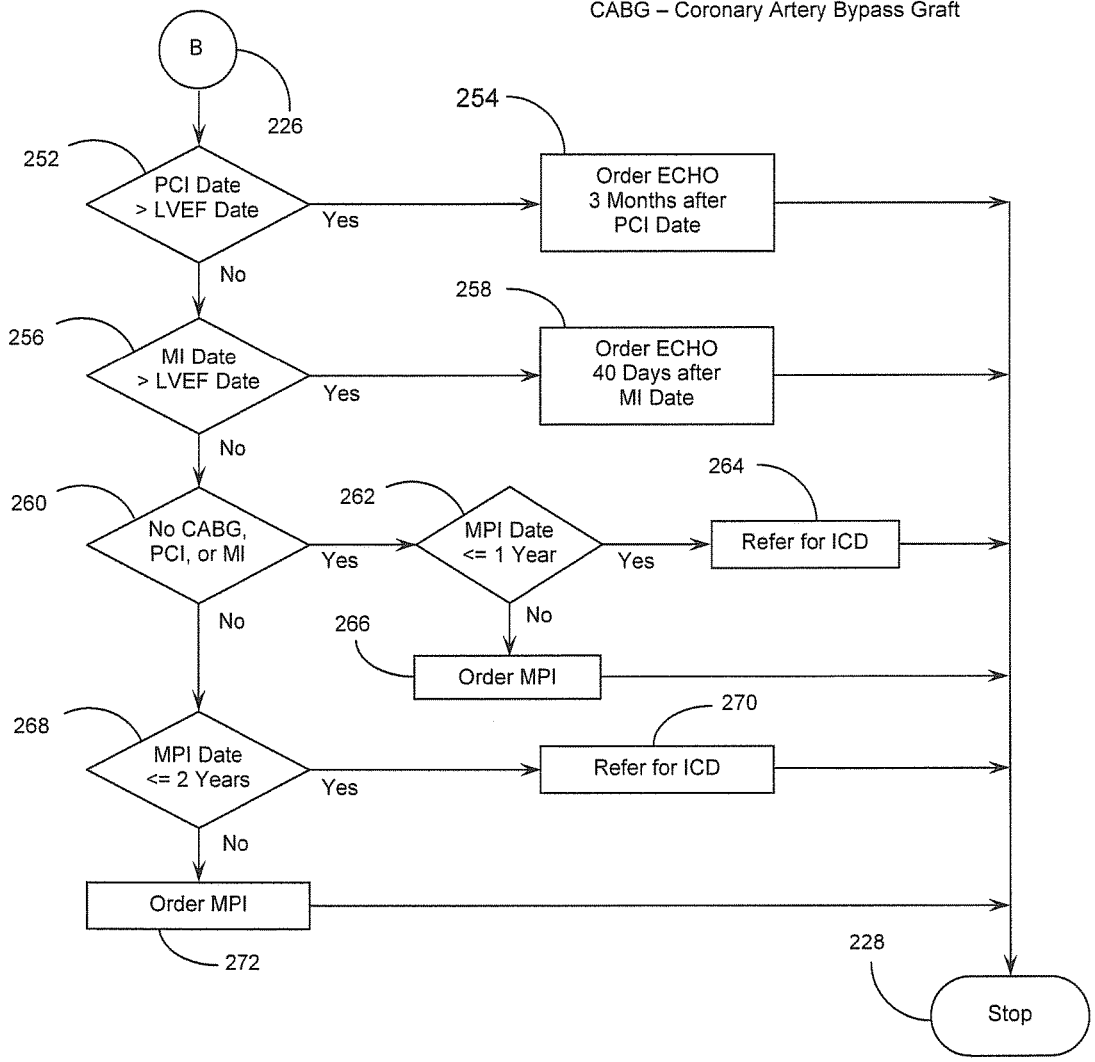
Figure 10:
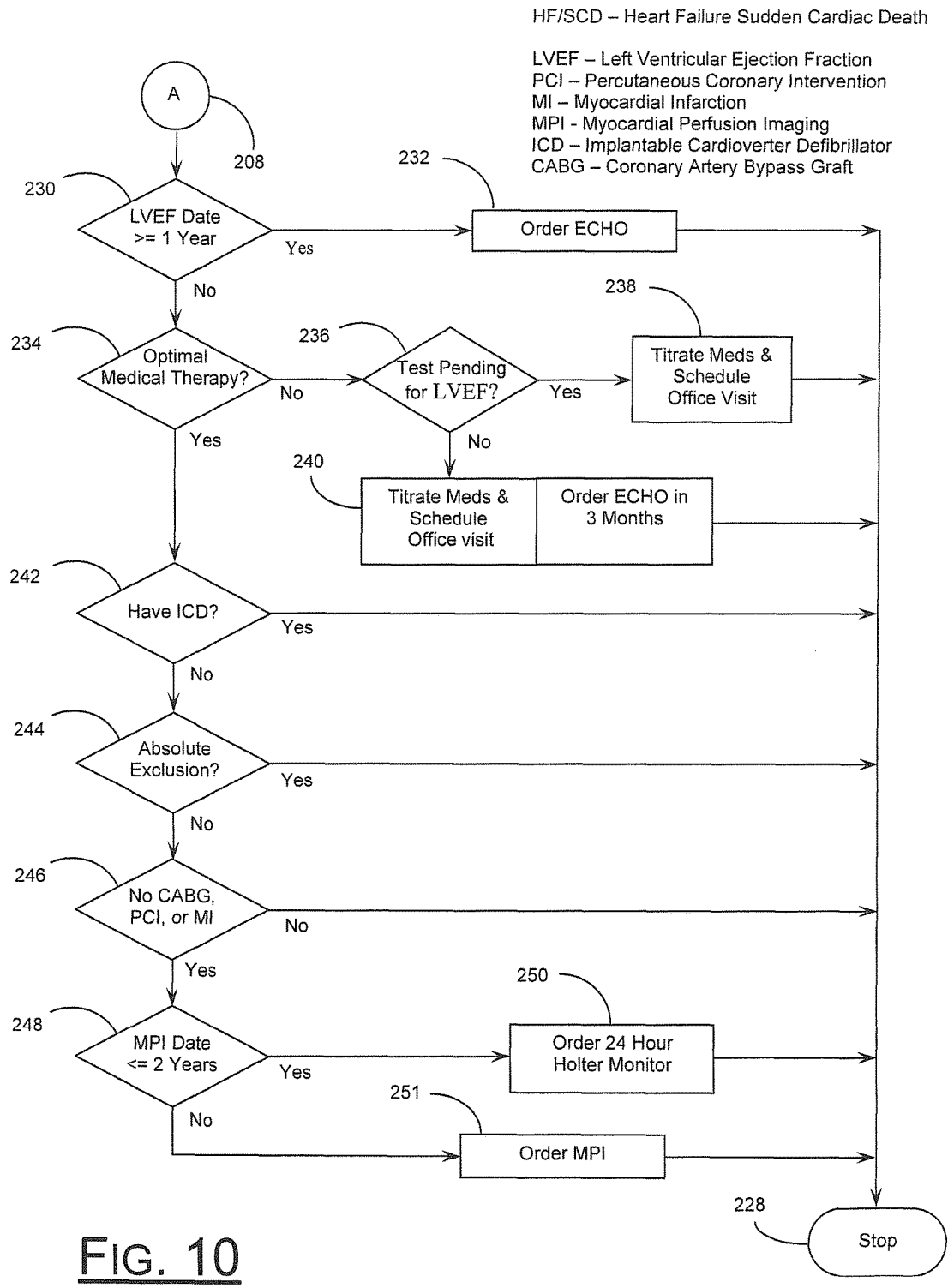

Particularly with reference to FIGS. 8-10, an alternative embodiment uses the SureCare software product to enable refined and alternative methodologies and systems that improve the information gathering aspect of preferred embodiments, as well as various patient preparation, counseling and other aspects of preferred embodiments. A specific implementation of the methods of the present invention is described in more detail with reference to FIGS. 8-10, which present the decision tree structure for a Heart Failure (HF)/Sudden Cardiac Death (SCD) procedure module.

This HF-SCD module embodiment is schematically described as beginning at Step 200 as shown in FIG. 8. It should be understood, however, that preferred embodiments further include installation and set-up of such procedural module in a manner that functionally interfaces with a facility's preferred process control systems (for reference, the "Pre-Existing Data Management System") and, preferably, its EMR system. Such installation and set-up preferably are performed by expert technicians in a series of meetings and discussions with facility management in order to discover the detail needs of the Pre-Existing Data Management System and to generally achieve a smooth integration with such pre-existing systems. Particular preferred embodiments are tailored for easy interface with popular data management EMR systems such as that commercialized under the "NextGen" designation, which uses a "knowledge-based model" with standardized data mapping to discrete data points, while customization may be needed to add any data points that are missing from the Pre-Existing Data Management System. Hidden data templates, audit trails, and other expedients may be provided to enable such initial set-up as will be evident to those of skill in the art.

Once the overall system has been integrated with other systems as desired, the process for a given patient then begins at Step 200. Upon initiation of the process at Step 200, particular designators are selected or entered to identify first whether the patient is a new patient or a prior patient, and prompts are provided to ensure a complete identification of the patient is captured in memory. Then, once the patient is identified with sufficient specificity, background data queries automatically gather relevant information from the Pre-Existing Data Management System for use during processing of the embodiment.

From initial Step 200, a series of query steps are executed, preferably in serial fashion, to gather sufficient information and/or to verify information already on file in the facility's or network's EMR system, as gathered by the background process mentioned previously. The extent of information required to be gathered or verified is determined by the software rules, as may be customized for specific classes of users and/or specific users, although the sufficiency is based on the object of ultimately recommending and/or completing the ordering process for relevant cardiac procedures, to be described further below. While the absence of sufficient data is characterized as a "Stop" condition at Stop 228, preferred embodiments allow procession of other query steps despite the "Stop" conditions, although it should be understood that ultimate results cannot be reached without remedying such "Stop" conditions.

When a new LVEF value is selected from the list, the care path will automatically reprocess using the new value and may alter the suggested order based on this new information More particularly, at Query Step 202 it is determined whether the date and other particulars of the last Left Ventricular Ejection Fraction (LVEF) measurement are available.

If at Query Step 204 it is determined that the LVEF is less than or equal to 35% then the process proceeds to Query Step 210 which asks whether the patient has an Implantable Cardioverter Defibrillator (ICD). If so, the process concludes at Stop 228. If not, the process proceeds to Query Step 212 which asks whether the patient represents an absolute exclusion. If so, the process concludes at Stop 228. If not, Query Step 214 asks whether the last LVEF date is 6 months or more ago. If yes, then at Step 216 an echo cardiogram (ECHO) is ordered and the process concludes at Stop 228.

A specific implementation of the methods of the present invention is described in more detail with reference to FIGS. 8-10, which present the decision tree structure for a Heart Failure (HF)/Sudden Cardiac Death (SCD) prevention/treatment module. This HF-SCD module is schematically described in the flowchart figures and begins at Step 200 as shown in FIG. 8. Initially it is determined whether the last Left Ventricular Ejection Fraction (LVEF) date is available at Query Step 202. If not, the process concludes at Stop 228. If the last LVEF date is available the process proceeds to Query Step 204 which asks whether the LVEF is less than or equal to 35%. If not, then Query Step 206 asks whether the LVEF is greater than 35% and less than or equal to 40%. If not, the process concludes at Stop 228. If the LVEF is greater than 35% and less than or equal to 40% then the process proceeds (through Connector A-Step 208) to further queries described in conjunction with FIG. 10 below.

If at Query Step 204 it is determined that the LVEF is less than or equal to 35% then the process proceeds to Query Step 210 which asks whether the patient has an Implantable Cardioverter Defibrillator (ICD). If so, the process concludes at Stop 228. If not, the process proceeds to Query Step 212 which asks whether the patient represents an absolute exclusion. If so, the process concludes at Stop 228. If not, Query Step 214 asks whether the last LVEF date is 6 months or more ago. If yes, then at Step 216 an echo cardiogram (ECHO) is ordered and the process concludes at Stop 228.

If at Query Step 214 it is determined that the last LVEF date is within the last 6 months then the process proceeds to Query Step 218 which asks whether the patient is on Optimal Medical Therapy (OMT) or treatment. If not, then at Step 220 the patient's medications are titrated (adjusted) and a further office visit is scheduled. The immediate process then concludes at Stop 228. If the patient is on OMT then the process proceeds to Query Step 222 which asks whether the LVEF was taken after any Coronary Artery Bypass Graft (CABG) that the patient may have had. If so, then at Step 224 an ECHO is ordered three months after the CABG date. The immediate process then concludes at Stop 228. If, at Query Step 222 it is determined that the LVEF was not taken after a CABG then the process proceeds (through Connector B-Step 226) to further queries described in conjunction with FIG. 8 below.

FIG. 8 shows the process that follows if at Query Step 222 (FIG. 7) it is determined that the LVEF was not taken after a CABG then the process proceeds (through Connector B-Step 226) to Query Step 252 which asks whether the LVEF was taken after a Percutaneous Coronary Intervention (PCI) that the patient may have had. If so, then at Step 254 an ECHO is ordered three months after the PCI date. The immediate process then concludes at Stop 228. If, at Query Step 252 it is determined that the LVEF was not taken after a PCI then the process proceeds to Query Step 256 which asks whether the LVEF was taken after a Myocardial Infarction (MI) event that the patient may have had. If so, then at Step 258 an ECHO is ordered forty days after the MI date. The immediate process then concludes at Stop 228.

If, at Query Step 256 it is determined that the LVEF was not taken after a MI event then the process proceeds to Query Step 260 which confirms whether there has been any of a CABG, PCI, or MI. If none of these have occurred then the process proceed to Query Step 262 which asks whether there has been a Myocardial Perfusion Imaging (MPI) test carried out in the last year. If not, then the process proceeds at Step 266 to call for an MPI. The immediate process then concludes at Stop 228. If there has been an MPI within the last year the process proceeds at Step 264 to refer the patient for an ICD. The immediate process then concludes at Stop 228.

If at Query Step 260 it is confirmed that there has been any occurrence of a CABG, PCI, or MI. then the process proceed to Query Step 268 which asks whether there has been a Myocardial Perfusion Imaging (MPI) test carried out in the last two years. If not, then the process proceeds at Step 272 to call for an MPI. The immediate process then concludes at Stop 228. If there has been an MPI within the last two years the process proceeds at Step 270 to refer the patient for an ICD. The immediate process then concludes at Stop 228.

Reference is next made to FIG. 9 which proceeds if, at Query Step 206, it is determined that the LVEF is greater than 35% and less than or equal to 40%. From Connector A-Step 208 the process proceeds through Query Step 230 which asks whether the LVEF date is a year or more ago. If so, then at Step 232 an ECHO is ordered. The immediate process then concludes at Stop 228. If at Query Step 230 it is determined that the LVEF date is less than a year ago then the process proceeds at Query Step 234 to ask whether the patient is on Optimal Medical Therapy (OMT) or treatment. If not, then Query Step 236 asks whether an LVEF test is pending. If so, then at Step 238 the patient's medications are titrated (adjusted) and a further office visit is scheduled. The immediate process then concludes at Stop 228. If an LVEF test is not pending then at Step 240 the patient's medications are titrated (adjusted), a further office visit is scheduled, and an ECHO in three months is ordered. The immediate process then concludes at Stop 228.

If the patient is determined (at Query Step 234) to be on OMT, then the process proceeds to Query Step 242, which asks whether the patient has an ICD. If so, then the process concludes at Stop 228. If the patient does not have an ICD then the process proceeds to Query Step 244 which asks whether the patient represents an absolute exclusion. If so, the process concludes at Stop 228. If not, Query Step 246 confirms whether there has been any of a CABG, PCI, or MI. If none of these have occurred then the process proceed to Query Step 248 which asks whether there has been an MPI test carried out in the last two years. If not, then the process proceeds at Step 251 to call for an MPI. The immediate process then concludes at Stop 228. If there has been an MPI within the last two years the process proceeds at Step 250 to order a 24 hour Holter Monitor for the patient. The immediate process then concludes at Stop 228.

Overview of the Process for Accessing a Specific Care Path

Implementation of the process described above is carried out through software driven query sessions involving the health care provider. The software provides evidence-based clinical information at the point of care. The rules engine associated with the software extracts patient data from a corresponding EMR system (and/or comparable database or network of databases) and creates suggested orders for physicians to consider in the management of heart and vascular disease (as an example). The patient care technician will typically access a symptoms information window for each patient encounter by selecting a "Symptoms" tab on the system user template. The Symptoms window would include questions to ask the patient; the first may relate (for example) to claudication symptoms and the rest to sleep patterns (for example) or the like. If additional data is needed for any of the care paths the Symptoms window will display a field to insert the missing data.

When the provider opens the patient's home page 300 within the system 10, the rules engine 20 will have automatically processed the data entered and if orders are recommended, or if data entry is required by the provider, a color-coded indicator will appear on the home page 300. Selecting this indicator will launch the specific system approval template 300. Additionally, if there are orders recommended or data entry required, the provider 490 will be redirected automatically to the approval template 300 the first time they open an order plan template 300. There is also preferably a link 300 provided on the order plan 300 template that allows access to the approval template 300 at any time.

The approval template has a section for each of the active care paths. The criteria used to generate recommendations can be viewed by clicking the "Criteria" links in each care path section or on the care path window templates (the HF-SCD for example). If any orders are recommended a brief description of the order will be provided in an action field, the status will be "Waiting Review" and there will be the opportunity to select either "Approve" or "Decline" the order for each care path. Some care paths may be slightly different as they do not suggest any order actions and instead provide a recommendation for patient care considerations.

The provider can "Agree" or "Ignore" the recommendation as appropriate. Accepting an action will automatically add the recommended orders to the patient's order plan for the encounter. Once an order has been accepted and entered, the "Accept" and "Decline" selections will no longer be displayed for that care path. An indicator of the order status will show on the corresponding care path section on the system template. When an order is declined, the system will prompt the provider for a reason with a data input window. The HF-SCD care path (as an example) provides two ways to decline an order: "Decline" and "Exclude". The "Exclude" selection also declines the order, but will display a data input window with choices to describe why the patient is being excluded from being processed by the care path. Selecting one of these choices will mark the patient's record with an absolute exclusion so the care path will not process on following patient visits. The provider can also enter absolute exclusions by opening the appropriate care path template window and selecting one of the exclusions listed. If the provider chooses to return to the order plan as a manner of leaving the Approval template, without either accepting or declining all of the recommended actions, they will be alerted that they will not be able to finalize and submit through the checkout template until all the outstanding suggested orders are addressed. All of the assessments need to be addressed before the provider will be able to finalize the encounter.

The Approval template provides access to the care path template windows by selecting the "Launch" link provided. Once launched, the HF-SCD care path may (for example) require the provider to answer questions about the patient's current status. If any specific data is required from the provider then the software system opens a query window that allows the provider to answer the question with a single step. Processing continues automatically as the provider answers the various queries presented. For example, the first question a provider may be required to answer is if the patient is on optimal tolerated medical therapy. If this question is answered "Yes" the patient's record will be flagged and the question will not be asked in future visits. If it is answered "No" the question will be asked again if appropriate.

A further detail question that the provider may need to answer to complete the processing of the HF-SCD care path is the patient's NYHA class. The system will check the NYHA Class field on the vital signs template and only prompt the provider for an answer if there is nothing entered in the field for the current encounter. Again, when an answer is selected, the care path will automatically continue processing. The NYHA Class query window will typically require documentation for each patient visit so that the care path system has the data to complete processing. In addition, the system provides (through a selectable information button on the software display) further information regarding the NYHA Class criteria.

As a further example of the decision making operation of the system, if the provider believes that the most recent Echo test (ECG) provided a reliable LVEF measurement then the selection tree set forth in the flowchart of FIGS. 8-10 may be launched. As part of this process the provider may select an EF history link to bring up a list of the patient's previous LVEF measurements. When a new LVEF value is selected from the list, the care path will automatically reprocess using the new value and may alter the suggested order based on the new information.

Alternative embodiments of certain aspects of the present invention also include adaptations of the methods and systems described above, such as adaptations to be used for providing a straightforward method and system by which a healthcare professional can determine whether, when and how any particular type of diagnostic test or medical procedure is indicated for any particular patient, or for any patient of a particular class of patients. Such alternatives include comparable adaptations such that adoption of the test, procedure will likely be accelerated among health care providers who are not intimately familiar with the health care issue being addressed or the process involved. While the various particular steps that would be useful in determining whether a patient is suited for a procedure will vary depending on the specific procedure, it will be evident to those of skill in the art whether and how systems and methods of the present method can be adapted for use with any particular procedures, or groups thereof.

Specific details are given in the above description to provide a thorough understanding of various preferred embodiments. However, it is understood that these and other embodiments may be practiced without these specific details. For example, circuits or processes may be shown in block diagrams in order not to obscure the embodiments in unnecessary detail. In other instances, well-known processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have many additional steps not included in the figure. A process may correspond to a method, a function, a procedure, a subroutine, a subprogram, etc. When a process corresponds to a function, its termination corresponds to a return of the function to the calling function or the main function.

Embodiments of the invention may involve use of a portable user interface that is adapted to provide or allow continuous or intermittent secure links with the facility network 400. For a middleware and/or other software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may be downloadable through an internet connection service. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

While the principles of the disclosure have been described above in connection with specific apparatuses and methods, it is to be clearly understood that this description is made only by way of example and not as limitation on the scope of the disclosure. Whether now known or later discovered, there are countless other alternatives, variations and modifications of the many features of the various described and illustrated embodiments, both in the process and in the system characteristics, that will be evident to those of skill in the art after careful and discerning review of the foregoing descriptions, particularly if they are also able to review all of the various systems and methods that have been tried in the public domain or otherwise described in the prior art. All such alternatives, variations and modifications are contemplated to fall within the scope of the present invention.

Although the present invention has been described in terms of the foregoing preferred and alternative embodiments, these descriptions and embodiments have been provided by way of explanation of examples only, in order to facilitate understanding of the present invention. As such, the descriptions and embodiments are not to be construed as limiting the present invention, the scope of which is limited only by the claims of this and any related patent applications and any amendments thereto.

What is claimed is:

1. A healthcare management system for determining an appropriate care path for a patient, said healthcare management system being associated with the care of patients having indications of heart failure and/or risks associated with sudden cardiac death, the system comprising:
   a. a healthcare facility network having a data management system comprising an EMR data management system that is adapted to securely store electronic medical records (EMR) of patients;
   b. identifiable memory locations for storing discrete data elements;
   c. one or more point of care electronic caregiver terminals that each have a caregiver display, said one or more point of care electronic caregiver terminals being in network communication with said EMR data management system;

d. data processors associated with said one or more electronic caregiver terminals; and
e. a programmed middleware system in electronic communication with said EMR data management system and said one or more point of care electronic caregiver terminals, wherein:
  i. said programmed middleware system is adapted to securely access EMR data stored by said EMR data management system and to extract pertinent data from said EMR data, said pertinent data relating to particularly identified patients;
  ii. said programmed middleware system is adapted to create readily-executable ordering options associated with cardiac care options for said particular patients;
  iii. said programmed middleware system is configured to operate through a graphic user interface having regions which allow an authorized user of said programmed middleware system to interact with said data management system of said healthcare facility network, said regions comprising graphical components including graphical fields, toolbars, and windows;
  iv. said programmed middleware system is adapted to convey an identification of a particular patient from said EMR data management system to said one or more point of care electronic caregiver terminals, said particular patient being a patient who is enrolled for receiving care through said healthcare facility network;
  v. said programmed middleware system being programmed to electronically access a data file in said EMR corresponding to the patient identification conveyed to said electronic caregiver terminal;
f. said programmed middleware system being programmed to then determine whether Left Ventricular Ejection Fraction (LVEF) test data is available and whether such data falls below a preset minimum value, within a preset range of values, or above a preset maximum value, and wherein said middleware system does not order any further care path if above the preset maximum value;
g. if the determination by the programmed middleware system is that the LVEF value is below the preset minimum value, then said programmed middleware system being further programmed to determine whether the patient has an Implantable Cardioverter Defibrillator (ICD), and wherein said programmed middleware system does not order any further care if the patient does have an ICD;
h. if the determination by the programmed middleware system is that the LVEF is below the preset minimum value and that the patient does not have an ICD, then said programmed middleware system being further programmed to determine if the patient meets the absolute exclusion criteria for receiving an ICD, and wherein said programmed middleware system does not order any further care path if the patient meets the absolute exclusion criteria;
i. if the determinations by programmed middleware system are that the LVEF value is below the preset minimum, the patient does not have an ICD, and the patient does not meet the absolute exclusion criteria, then said programmed middleware system being further programmed to determine whether the LVEF test occurred within the last six months, and if not, said middleware system being further programmed to order an echocardiogram;
j. if the determinations by the programmed middleware system are the same as (i), above, and that the LVEF test did occur within the last six months, then said programmed middleware system being programmed to determine whether Optimal Medical Therapy (OMT) is in place, and if not, said programmed middleware system being further programmed to titrate the medications of the patient and schedule a further evaluation;
k. if the determinations by the programmed middleware system are the same as (j), above, and the OMT is in place, then said programmed middleware system being programmed to determine whether a Coronary Artery Bypass Graft (CABG) has been performed; a Percutaneous Coronary Intervention (PCI) has been performed; and/or a Myocardial Infarction (MI) has occurred, and if so, whether such were performed or occurred before the LVEF test, and if not, said programmed middleware system being further programmed to order an echocardiogram within a preset time period after the CABG or PCI performance, or the MI occurrence;
l. if the determinations by the programmed middleware system are the same as (k), above, and that none of a CABG, PCI, or MI has been performed or has occurred, or been performed or occurred before the LVEF test, then said programmed middleware system being programmed to determine whether a Myocardial Perfusion Imaging (MPI) test has been made within the last year, and if so, said programmed middleware system being further programmed to refer the patient for an ICD, and if not, said programmed middleware system being further programmed to order an MPI; and
m. if the determination by the programmed middleware system is that the LVEF value is within a preset range, then said programmed middleware system being programmed to proceed through a first alternate care path.

2. The healthcare management system according to claim 1 wherein the first care path comprises:
a. said programmed middleware system being programmed to determine whether the LVEF test occurred within the last year, and if not, said programmed middleware system being further programmed to order an echocardiogram;
b. if the determination made in (a), above, is that the LVEF test did occur within the last year, then said programmed middleware system being programmed to determine whether Optimal Medical Therapy (OMT) is in place;
c. if the determination made in (b), above, is the OMT is not in place then said programmed middleware system being programmed to determine if a LVEF test is pending, and if so, said programmed middleware system being further programmed to titrate the medications of the patient and schedule a further evaluation, and if not, said programmed middleware system being further programmed to titrate the medications of the patient, order an echocardiogram, and schedule a further evaluation;
d. if the determination made in (b), above, is that OMT is in place, then said programmed middleware system being programmed to determine whether the patient has an Implantable Cardioverter Defibrillator (ICD), and wherein said programmed middleware system does not order any further care path if the patient does have an ICD;

e. if the determination made in (d), above is that the patient does not have an ICD, then said programmed middleware system being programmed to determine if the patient meets the absolute exclusion criteria for receiving an ICD and wherein said programmed middleware system does not order any further care path if the patient meets the absolute exclusion criteria;

f. if the determination made in (e), above, is made, and OMT is in place, then said programmed middleware system being programmed to determine whether any of a Coronary Artery Bypass Graft (CABG) has been performed, a Percutaneous Coronary Intervention (PCI) has been performed; and/or a Myocardial Infarction (MI) has occurred, and wherein said programmed middleware system does not order any further care path if so; and g. if the determination of (f), above, is made, and if none of a CABG, PCI, or MI has been performed or has occurred, then said programmed middleware system being programmed to determine whether a Myocardial Perfusion Imaging (MPI) test has been made within the last two years, and if so, said programmed middleware system being further programmed to order a 24-hour Holter monitor for the patient, and if not, said programmed middleware system being further programmed to order an MPI.

3. The healthcare management system of claim 2 wherein said absolute exclusion criteria are selected from the group consisting of severe end stage cardiomyopathy, severe end stage Chronic Obstructive Pulmonary Disease (COPD) with oxygen dependence, severe dementia, metastatic cancer, extensive neurological defects, irreversible brain damage from preexisting cerebral disease, any disease other than cardiac disease associated with a likelihood of survival less than one year, patient refusal of an ICD implant, and combinations thereof.

4. The healthcare management system of claim 2 wherein referral of the patient for the ICD comprises the programmed middleware system being programmed to provide said patient with educational materials concerning the ICD.

5. A healthcare management system for determining an appropriate care path for a patient having indications of heart failure and/or risks associated with sudden cardiac death, the healthcare management system comprising:

a. a healthcare facility or network having a data management system that is adapted to store electronic medical records (EMR) of patients;

b. identifiable memory locations for storing discrete aspects of said EMR for particular patients;

c. one or more point of care electronic caregiver terminals;

d. data processors associated with said one or more electronic caregiver terminals;

e. a programmed middleware system in electronic communication with said EMR system and said one or more point of care electronic caregiver terminals;

f. said one or more point of care electronic caregiver terminals being adapted to receive an identification of a particular patient who is enrolled for receiving care through said healthcare facility or network from said EMR system via said programmed middleware system;

g. said programmed middleware system being programmed to electronically access a data file in said EMR system corresponding to the patient identification received by said electronic caregiver terminal;

h. said programmed middleware system being programmed to determine whether Left Ventricular Ejection Fraction (LVEF) test data is available;

i. if the determination made by the programmed middleware system is that the LVEF test data is not available, then said programmed middleware system being further programmed to not recommend any further care path;

j. if the determination by the programmed middleware system is that LVEF test data is available, then said programmed middleware system being programmed to determine whether the LVEF test data is less than or equal to a preset minimum value;

k. if the determination by the programmed middleware system is that the LVEF test data is less than or equal to the preset minimum value, then said programmed middleware system being further programmed to proceed through a first care path;

l. if the determination by the programmed middleware system is that the LVEF test data is not less than or equal to the preset minimum value, then said programmed middleware system being programmed to determine whether the LVEF test data is less than or equal to a preset maximum value;

m. if the determination by the programmed middleware system is that the LVEF test data is less than or equal to the preset maximum value, then said programmed middleware system being further programmed to proceed through a second care path; and n. if the determination by the programmed middleware system is that the LVEF test data is not less than or equal to the preset maximum value, then said programmed middleware system being further programmed to not recommend any further care path.

6. The healthcare management system of claim 5 wherein the preset minimum value for the LVEF test data is 35% and the preset maximum value for the LVEF test data is 40%.

7. The healthcare management system of claim 5 wherein the preset minimum value for the LVEF test data is 30%.

8. The healthcare management system of claim 5 wherein, if the determination by the programmed middleware system is that the LVEF test data is not available, then said programmed middleware system being programmed to order an echocardiogram or a Multigated Acquisition (MUGA) scan prior to not recommending any further care path.

9. The healthcare management system of claim 5 wherein the second care path comprises:

a. said programmed middleware system being programmed to determine whether the LVEF test occurred within the last year, and if not, said programmed middleware system being further programmed to order an echocardiogram;

b. if the determination by the programmed middleware system is that the LVEF test did occur within the last year, then said programmed middleware system being programmed to determine whether Optimal Medical Therapy (OMT) is in place;

c. if the determination by the programmed middleware system is that OMT is not in place, then said programmed middleware system being programmed to determine if an LVEF test is pending, and if so, said programmed middleware system being further programmed to titrate medications of the patient and schedule a further evaluation, and if not, said programmed middleware system being further programmed to titrate the medications of the patient, order the echocardiogram, and schedule the further evaluation;

d. if the determination by the programmed middleware system is that OMT is in place, then said programmed middleware system being programmed to determine whether the patient has an Implantable Cardioverter Defibrillator (ICD), and wherein said programmed middleware system does not recommend any further care path if the patient does have the ICD;

e. if the determination by the programmed middleware system is that the patient does not have the ICD, then said programmed middleware system being programmed to determine if the patient meets absolute exclusion criteria for receiving the ICD, and wherein said programmed middleware system does not recommend any further care path if the patient meets the absolute exclusion criteria;

f. if the determination made by the programmed middleware system is that the patient does not meet the absolute exclusion criteria for receiving the ICD, then said programmed middleware system being programmed to determine whether a Coronary Artery Bypass Graft (CABG) has been performed; a Percutaneous Coronary Intervention (PCI) has been performed; or a Myocardial Infarction (MI) has occurred, and if so, said programmed middleware system does not recommend any further care path;

g. if the determination made by the programmed middleware system is that none of the CABG, PCI, or MI has been performed or has occurred, then said programmed middleware system being programmed to determine whether a Myocardial Perfusion Imaging (MPI) test has been performed within the last two years, and if so, said programmed middleware system being further programmed to order a 24 hour Holter Monitor for the patient, and if not, said programmed middleware system being further programmed to order an MPI.

10. The healthcare management system of claim 9 wherein said absolute exclusion criteria are selected from the group consisting of severe end stage cardiomyopathy, severe end stage Chronic Obstructive Pulmonary Disease (COPD) with oxygen dependence, severe dementia, metastatic cancer, extensive neurological deficits, irreversible brain damage from preexisting cerebral disease, any disease other than cardiac disease associated with a likelihood of survival less than one year, patient refusal of an ICD implant, and combinations thereof.

11. The healthcare management system of claim 5, further comprising said programmed middleware system being programmed to determine if the patient has a temporary exclusion.

12. The healthcare management system of claim 11 wherein said temporary exclusion is selected from the group consisting of non-ischemic dilated cardiomyopathy, class II or III Congestive Heart Failure (CHF), myocardial infarction within the past forty days, Coronary Artery Bypass Graft (CABG) or Percutaneous Transluminal Coronary Angioplasty (PCTA) within three months, Ischemic Cardiomyopathy (ICM) with no ischemic workup within 12 months, suspected or possible severe carotid disease, absence of beta blocker or Ace inhibitor/Angiotensin Receptor Blocker (ARB), that the patient is currently being titrated on beta blocker, and combinations thereof.

13. The healthcare management system of claim 5, further comprising said programmed middleware system being programmed to determine if the patient has a relative exclusion.

14. The healthcare management system of claim 13 wherein said relative exclusion is selected from the group consisting of severe diabetes with end organ complications, End Stage Renal Disease (ESRD) on dialysis, paraplegia or previous cerebral vascular accident (CVA), that the patient is over eighty-five years of age but still fairly active mentally and physically, and combinations thereof.

\* \* \* \* \*